(12) United States Patent
Siegrist

(10) Patent No.: US 11,726,229 B2
(45) Date of Patent: Aug. 15, 2023

(54) TEST DEVICE FOR IRRADIATING PRODUCTS ON A CONVEYOR ROUTE

(71) Applicant: Wipotec GmbH, Kaiserslautern (DE)

(72) Inventor: Michael Siegrist, Kaiserslautern (DE)

(73) Assignee: Wipotec GmbH, Kaiserslautern (DE)

( * ) Notice: Subject to any disclaimer, the term of this patent is extended or adjusted under 35 U.S.C. 154(b) by 563 days.

(21) Appl. No.: 16/801,498

(22) Filed: Feb. 26, 2020

(65) Prior Publication Data

US 2020/0275683 A1 Sep. 3, 2020

(30) Foreign Application Priority Data

Mar. 1, 2019 (DE) .......................... 102019105309.9

(51) Int. Cl.
*G01V 5/00* (2006.01)
*G01G 19/00* (2006.01)

(52) U.S. Cl.
CPC .............. *G01V 5/00* (2013.01); *G01G 19/00* (2013.01)

(58) Field of Classification Search
None
See application file for complete search history.

(56) References Cited

U.S. PATENT DOCUMENTS

| 6,872,001 B1 | 3/2005 | Gilevich |
| 9,869,642 B2 * | 1/2018 | Duppre ................. G01N 23/083 |
| 2012/0073415 A1 * | 3/2012 | Maidel ...................... B26D 5/32 |
| | | 426/531 |
| 2014/0170274 A1 | 6/2014 | Duppre |
| 2015/0338355 A1 | 11/2015 | Kim et al. |
| 2019/0351804 A1 * | 11/2019 | Kanck ................... G01N 33/24 |

FOREIGN PATENT DOCUMENTS

| DE | 102010034674 A1 | 2/2012 |
| EP | 2711701 A1 | 3/2014 |
| EP | 2887056 A1 | 6/2015 |
| JP | H09127021 A | 5/1997 |
| JP | H1062362 A | 3/1998 |
| JP | 2002243665 A | 8/2002 |
| JP | 2006084275 A | 3/2006 |
| JP | 2009168590 A | 7/2009 |
| JP | 2014062906 A | 4/2014 |

OTHER PUBLICATIONS

Japan patent application No. 2020-030378 Office Action dated Mar. 17, 2021.
DE 102019105309.9 Office action dated Jun. 14, 2019.
Second Office Action dated Nov. 22, 2021 in Japanese patent application No. 2020030378.
Extended European Search Report dated Sep. 7, 2020 in EP 20158836.5.

* cited by examiner

*Primary Examiner* — Hoon K Song
(74) *Attorney, Agent, or Firm* — The Culbertson Group, P.C.

(57) ABSTRACT

A test device for the irradiation of products which are fed into a housing along at least two tracks. At least one separate sensor is provided for each track in order to separately monitor the arrival at a target position selected individually for each track preferably within the housing of the test device.

19 Claims, 1 Drawing Sheet

TEST DEVICE FOR IRRADIATING PRODUCTS ON A CONVEYOR ROUTE

TECHNICAL FIELD OF THE INVENTION

The present invention involves a test device for irradiating products and a process for using such a device.

BACKGROUND OF THE INVENTION

In the industrial production of products, in particular food products, a test device for irradiating products is frequently provided in order to verify the proper consistency or to be able to detect foreign bodies. Irradiation with x-rays is offered for this purpose (throughout this disclosure and the accompanying claims the term "x-ray" is meant to be representative of other irradiation processes as well). Such irradiation-type testing devices not only must ensure the highest possible product throughput but also prevent an evaluating x-ray from irradiating more than one product at the same time, for example if they overlap along the x-ray beam. In the case of irradiating more than one product at the same time, foreign bodies cannot be assigned to a product with certainty.

For reasons of x-ray protection, the irradiation-type testing device includes a housing which needs to protect against the unintended emission of x-rays during the irradiation of the product made available in the housing or seal it off, for example with a bulkhead. The bulkhead can optionally close or open an input opening in the housing such that when the bulkhead is opened, products can be inserted in the housing. Expediently, the products are fed along several tracks on the test device, which as a rule are parallel to each other or moved into the interior of the housing through the input opening. Once the product intended for irradiation has passed entirely through the opening, the bulkhead can be closed in order to start the irradiation.

In well-known practice in this respect, when products are fed in on multiple tracks it can also occur that one product is already located completely within the housing while a product on another track has not passed entirely through the opening to the housing. The bulkhead cannot be closed and the product already located in the housing cannot be moved further or irradiated. This can result in a time delay to the production process or even a safety risk, which is to be avoided.

SUMMARY OF THE INVENTION

According to one aspect of the present invention, where products are transported on multiple tracks a separate sensor can be assigned to every track. This separate sensor can detect when the product moved on the respective track has arrived at a predetermined target position along the conveyor route. Thus, it can be ensured for every track that one of the products moved along it has arrived at one of the specified target positions in the housing for the test device, and then the process steps can be carried out safely.

In particular, the products can be oblong bars of food (blocks of cheese, strands of sausages, etc.). In principle, the device and the process are also suitable for irradiating other products that are either in a shape-stable form or can be transported on the relevant tracks in suitable containers.

Products are sent to a test device according to the invention along at least two tracks, each track fed in sequence, whereby the tracks preferably run parallel to each other along a conveyor route and each track has at least its own means of propulsion in the housing in order to individually transport the product on the respective track. According to the invention, at least one separate sensor is assigned to each track in order to detect when the product moved on the respective track has reached a predetermined target position along the conveyor route. Based on this, the irradiation of the products can be initiated as an additional process step. In particular, the first sensors should allow for a decision to be made on whether a product is ready for the subsequent irradiation within the housing and/or the housing opening is unblocked so that the bulkhead can be closed.

By contrast, just a single sensor monitoring all tracks jointly (for example, a light cabinet directed across the tracks) only with great effort can provide information on which product (more specifically, on which track) is still blocking the opening to the housing or if a forward target position where the irradiation is to start was not yet reached. The allocation of individual sensors to each track according to the invention makes this cost-effective and quickly possible.

Preferably, the target position monitored by the first sensors for each track is within the housing and borders on an irradiation zone in which the products can be irradiated in the previously described manner. If the front edge of a product transported on a track reaches this target position, then using the known length of the product (measured in the transport direction) it can be concluded whether the back end of the product was completely moved into the housing through the housing opening. If this applies to all tracks used for conveying, then all products have cleared the opening to the housing so that the bulkhead can be closed for the subsequent irradiation of the products to start.

In one implementation of the invention, the product for every track is first moved far enough to reach the target position and recorded by the associated sensor. Then the product is stopped. It is located directly in the target position and, when the length in the conveying direction is known, sufficiently far in the housing in order to not block the bulkhead. The additional tracks are operated in the same manner. After operating the tracks accordingly, all the frontmost products are positioned in the target position on the tracks used for conveying and the bulkhead can be closed. In some implementations, each product can be moved backward slightly after reaching the target position. The individual first sensors are then released for further process steps in which for example the repeat passing of this and additional sensors is recorded and is taken into consideration in the process control.

Per the requirements on the results of the irradiation, the products can be transported one after the other or in groups through the x-ray beam oriented downstream of the target position. After ending the irradiation, the housing can be reopened in the transport direction downstream at a bulkhead in order to move the products out of the test device. The input side bulkhead can likewise be opened again in order to move additional products, which are fed into the interior of the housing on the individual tracks.

The target position is preferably located far enough in the housing that the products arriving there no longer block the input side bulkhead. However, it is also conceivable to place the target position closer to the input side bulkhead or the housing wall in order to satisfy other monitoring requirements. Also, the target position need not match the position of the respective first sensor. Depending on the type of sensor, the sensors can also monitor a position spaced at a distance from a sensor.

According to some implementations, a test device includes in addition to the first sensor per track respectively at least a second, separate sensor for each track in order to monitor a test position different from the target position along the conveyor route. The second sensor for each track can be designed functionally or structurally similar to the first sensor. By arranging at least two sensors along every track, a maximum or minimum length for example can be verified for a product without comparison with an encoder, which then accelerates or optimizes the process for an x-ray sequence. At the same time, it can be determined whether a front-most product along a track is followed unexpectedly or at too short a distance by another product, wherein the distance can be appropriately defined or verified by the placement of the first and second sensors.

Idle tracks can also, in accordance with the invention, easily be detected by the individual track monitoring such that there is no need to wait for the arrival of a product at the target position on this track. The next irradiation can be done accordingly more quickly.

Implementations of a test device in accordance with the present invention may include an irradiation source, in particular an x-ray source, in order to be able to irradiate the products. Such a test device also includes a housing in which the irradiation source is situated and which can be secured in a suitable manner against the unintended emission of x-rays. At least two tracks along which products are to be moved into the housing for the test device run through a closeable input opening on the housing to the interior and may lead out of the housing to a different location. The target position is therefore located within the housing. If the target position on all tracks used for conveying is reached by the products there, the housing opening is accordingly assumed to be "free" and can be closed by a radiation-safe bulkhead in order to start irradiation of the products. If the length of the product is not known, then at minimum it can be ensured by at least a second sensor which monitors a test position different from the target position that the product has, for example exited the test position. If the test position is close to the housing input opening, for example, just inside the housing, then at least a second sensor, or a second sensor provided for this purpose for each track, can signal when the housing input opening is free, regardless of whether the respective product has already reached the downstream target position. As a result, the closing of the bulkhead can already be started when at least one of the two or both second sensors signal that the housing opening is free, while at the same time all products already located within the housing can still be moved on to the target position. This reduces the processing time.

In order to be able to move the product within the test device housing, a separate means of propulsion is provided for each track. For this purpose this means of propulsion, which can be designed as conveyor belts, chains, or other means of transport known to one skilled in the art, may be located as close as possible to the inside of the housing input opening in order to be able to accept the products fed in from the outside as easily as possible.

Other embodiments of the invention may provide a means of propulsion outside of the housing for the test device as well. A product can first be moved forward along a selected track with the means of propulsion located outside of the housing. With an input opening bulkhead in its open position, the external means of propulsion delivers the product through the input opening to the means of propulsion located in the housing on the same track which fully accepts the product by transporting it forward and moving it into the housing.

According to some variations of the invention, the means of propulsion provided outside of the housing is designed as a single means of transport for all tracks, such as a conveyor belt wide enough to stretch over all tracks. All products are then moved on individual tracks to the housing but at the same time. With the separately designed drive in accordance with the invention inside of the housing, incorrect positioning on the conveyor belt can be compensated and the products positioned individually for each track.

Both the means of propulsion located within the housing and the means of propulsion located outside of the housing may be individually operable for each track in order to be able to move the products independent of the adjacent tracks. This solution also allows for a previous product on a track in the housing to be moved in, for example up to the target position, while a following product on the same track outside of the housing can be independently moved up to the housing in order to be ready for the next irradiation process. Preferably, the means of propulsion is also operable such that the respective product can be transported backwards, meaning against the actual transport direction.

Although each means of propulsion can be operable and controllable using a separate motor, a variation is also conceivable in which a motor is provided for several tracks, which can be individually coupled to and uncoupled from the motor (for example, with a motor shaft). This reduces the design effort and costs.

According to some embodiments of the invention, the test device also comprises a scale in order to record the weight of the products transported along the tracks. The scale can advantageously be designed as a multi-track scale. However, the products can alternatively be separated and then fed to the scale one after the other or fed together and then individually moved forward (differential weighing). The scale, viewed in the transport direction, can be placed upstream or downstream from the irradiation.

Test devices in accordance with the invention may include a control unit in order to control in particular the means of propulsion for the individual tracks. The preferably automated opening and closing of the housing opening and the operation of the x-ray source can also be controlled by the control unit, which may also be designed to record and evaluate the signals from the individual sensors. A scale integrated into the test device can also be controlled by such a higher-level control unit. Of course, the control unit can have additional interfaces for exchanging date or for network connectivity.

Processes in accordance with the invention for operating the previously described test device may include the following steps:

First, products are moved forward along the conveyor route on at least two tracks independent of each other to a test device in accordance with the invention, for example using a means of propulsion located outside of the housing for the test device, which is individually controllable for each track.

Along the conveyor route at least one target position is determined for each track, for which a separate sensor is provided for each track to monitor when a product conveyed along the track arrives.

The movement is interrupted along that track for which the assigned first sensor signals the arrival at the target position by the product moved along the respective track.

This process allows the monitoring of the individual tracks to determine whether a product moved there has reached a certain position along the conveyor. Preferably, the target position is located within the housing for the test device and adjacent to the irradiation zone. The completion of the process can then comprise that the front-most product on every track is moved forward up to the target position so as then to interrupt the respective transport and—optionally—to move the product back a small amount.

If the target position is located far enough in the housing that even the longest product expected can no longer protrude through the housing opening with its back end when the front end has reached the target position, then it is sufficient for the housing to close safely and the irradiation of the products to begin.

This process can furthermore comprise at least one of two sensors which jointly for all tracks or as a group of individual sensors monitor one test position per track downstream or—preferably—upstream from the housing opening and thereby monitor inside the housing. These second sensors are preferably evaluated for monitoring of the back end of the conveyed products. The second sensors could for example be located immediately adjacent to the housing input opening inside the housing, whereby in each case a second sensor is assigned to each track. If such a sensor does not detect a product in its coverage area, this can be evaluated as an indication that no product is protruding through the housing opening on the track in question. This applies to all tracks in use so that the housing can be closed and regardless of whether the front end of product has arrived at the target position defined further inside the test device. The further transport of the products within the test device up to the relevant arrival at the target position can be done to save time while the housing is closing or already closed.

The irradiation of the individual products can be done by moving the product on a first track through the target position in the direction of movement through the x-ray while the x-rays irradiating the product are recorded and evaluated. If the product on the first track has fully passed through the x-ray beam, then the second product can be moved through the x-ray beam and so on. If the irradiation and the associated evaluation permit, several products can also be moved through the preferably fanned out x-ray beam at the same time. After the irradiation of all products ends, the products may exit the test device through an additional housing opening and be fed to another processing station. The input opening can also be released again by removing the bulkhead in order to move the next products located upstream and outside of the housing on each track into the housing.

These and other advantages and features of the invention will be apparent from the following description of representative embodiments, considered along with the accompanying drawings.

DESCRIPTION OF REPRESENTATIVE EMBODIMENTS

Figure 1:
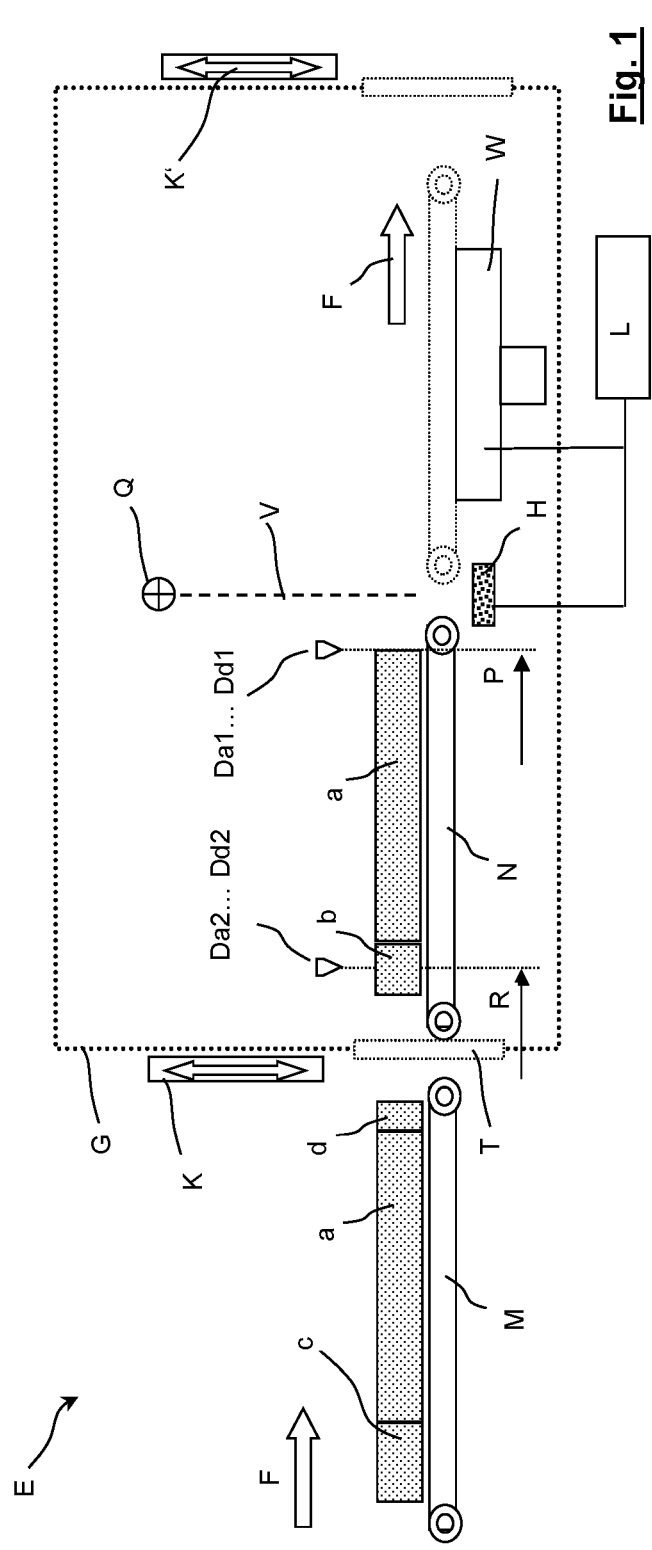
FIG. 1 shows a schematic side view of an opened test device.

FIG. 1 shows a simplified, cross-sectional side view of a test device E in accordance with the invention. Test device E comprises a radiation-safe housing G, within which an x-ray source Q is designed to output a fan-shaped x-ray beam V. X-ray beam V irradiates the products a, b, c, d, etc., when they pass it. Preferably, x-ray source Q is only active for this time period and housing G is closed then. The irradiation is recorded by recording unit H and forwarded in converted form to a higher-level controller L for further evaluation.

Products a, b, c, d, etc. are then fed to housing G along several tracks Sa, Sb, Sc, and Sd along a conveyor F aligned with said tracks. The tracks are located one behind the other in the view according to FIG. 1; their arrangement next to each other can be seen in the simplified top view according to FIG. 2. "Track" does not necessarily mean a physical component; rather, this term is meant to describe an individual transport path that is realized in design by a suitable means of conveyance or propulsion, for example a belt, possibly with side guiding elements. According to FIGS. 1 and 2, each of the tracks Sa, Sb, Sc, and Sd comprises at least two means of propulsion M and N, each made separate from the other. Within the housing G are four conveyor belts serving as said means of propulsion, each of which can move a product in transport direction F within housing G. Outside of housing G, and each aligning with the means of propulsion N located within housing G, separate conveyor belts, which are upstream of means of propulsion N and housing G, are provided as means of propulsion M for each track. (In a simplified embodiment, only a single conveyor belt M is provided to serve all tracks jointly). Means of propulsion M is used to feed individual products along the relevant track to housing G in transport direction F and deliver through an input opening T to the respective means of propulsion N within the housing. (In the transport direction to means of propulsion N, additional means of propulsion can be subsequently provided in order to be able to move the irradiated products jointly or in every track individually or from housing G. This is only indicated in FIG. 1.)

Each means of propulsion M and N can have a separate motor. Alternatively, a motor that jointly serves several means of propulsion M and/or N is conceivable, which drives the individual means of propulsion using controllable couplings. The means of propulsion or their motors can be controlled, for example, with the control unit.

An individual sensor Da1, Db1, Dc1, Dd1, is provided along each of the tracks in the interior of housing G at target position P for each track. Target position P is located close to the position of x-ray beam V. The first sensors Da1, Db1, Dc1, Dd1 are used to detect the arrival of the front-most edge of the individual products a, b, c, d at target position P and, depending on this, to interrupt the further transport of the relevant product by the associated means of propulsion N. The placement of a second sensor Da2, Db2, Dc2, Dd2 is provided close to housing opening T inside housing G, wherein each sensor is assigned to one of the tracks. These sensors are used in particular to detect that a product has been completely inserted in housing G and thus opening T is no longer blocked, in order in this case to be able to close opening T on housing G with a radiation-safe bulkhead K. Means of propulsion M, on which subsequent products are moved outside of housing G, is then controlled accordingly so that none of its products are moved up against closed bulkhead K.

After closing bulkhead K, the irradiation of the individual products already located inside the housing can be done by moving them in sequence or partially or entirely at the same time through x-ray beam fan V. After completing the irradiation, the products (once again, in sequence or jointly) can be moved through a second opening which is closeable with second bulkhead K' and out of housing G using suitable means of conveyance. Outside or inside of housing G, a scale W can be provided in order to record the weight of products a, b, c, d individually or as a group. Scale W can also be connected to control unit L for the exchange of data. Control unit L can be located within, but preferably outside of, housing G for this purpose.

The test device in accordance with the invention can be used as follows:

Products a, b, c, d, etc. are fed to housing G in test device E along tracks Sa, Sb, Sc, and Sd in transport direction F. The products fed along track Sa are labeled with "a", those on track Sb with "b", and so on.

When bulkhead K is open, a front-most product viewed in direction of conveyance F can be moved in any track through housing opening T in the housing G for test device E. For this purpose, means of propulsion N within housing G accepts the products introduced outside of housing G by means of propulsion M. Each means of propulsion N is thus controlled so that the relevant conveyed product arrives with its front edge at a target position monitored by sensors Da1, Db1, Dc1, Dd1 and then is preferably stopped. The second sensors Da2, Db2, Dc2, Dd2 can be used to monitor whether the back end of any product was conveyed far enough into housing G such that opening T is unblocked and ready to be closed by bulkhead K. (If a product arrives at a target position after the bulkhead has already closed, depending on the process specifications it could be moved directly without interruption through the target position for irradiation in order to save time).

Figure 2:
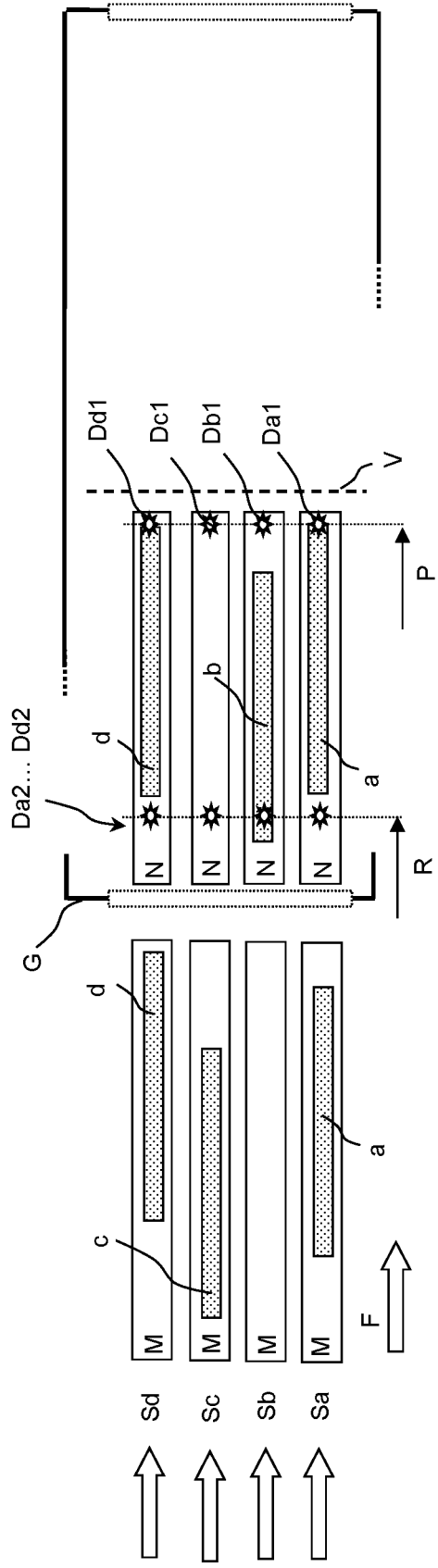
FIG. 2 shows a schematic top view of the test device according to FIG. 1.

In FIG. 2, products a and d shown as examples have arrived at target position P. Product b on track Sb has not arrived at target position P nor cleared test position R. The result of evaluation by at least sensor Db2 would be that bulkhead K must wait to close. On track Sc no product was previously moved into housing G. Product c moved closer outside of housing G in track Sc can be moved forward for this purpose. Alternatively (possibly for time optimization), track Sc can remain empty for the current irradiation cycle, so that the next product c made available outside of the housing is moved into the housing for the next irradiation cycle.

Once all products intended for irradiation have arrived at the front target position P, or at least have cleared test position R, bulkhead K can be closed in order to then perform irradiation of the products. Of course, second bulkhead K' if present may also be closed during the irradiation. During this irradiation, additional products can be moved closer to the housing with suitable control of means of propulsion M and made available near the housing for the next irradiation cycle. For this purpose, additional sensors not described in greater detail can be used to record the product movement in the individual tracks.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

REFERENCE SYMBOLS a, b, c . . . products
D2, Da2, Db2, Dc2, Dd2, etc. second sensor
Da1, Db1, Dc1, Dd1, etc. first sensor
E Test device
F conveyor route
G housing
H recording unit
K, K' bulkhead
M second means of propulsion
N first means of propulsion
P target position
Q source of radiation
R test position
Sa, Sb, Sc, Sd, etc. tracks
T opening
V x-ray beam
W scale

The invention claimed is:

1. A test device including:
   (a) a source of radiation for irradiating products, the source of radiation being operable for producing an irradiation beam directed along a beam path from the source of radiation to a recording unit;
   (b) a housing with at least one closeable opening, wherein the beam path is within the housing and wherein the products are fed into the housing along two tracks extending along a conveyor route, each track being associated with a respective first means of propulsion in the housing, each respective first means of propulsion being operable to convey a respective one of the products within the housing along the respective track with which that respective first means of propulsion is associated; and
   (c) each track having associated therewith a respective first sensor, each first sensor being operable to detect when a product moved on the respective track with which that first sensor is associated has arrived at a target position in the housing along the conveyor route.

2. The test device of claim 1 wherein:
   (a) the products are fed into the housing along at least one additional track extending along the conveyor route, each additional track being associated with a respective additional first means of propulsion in the housing, each respective additional first means of propulsion being operable to convey a respective one of the products within the housing along the respective additional track with which that respective additional first means of propulsion is associated; and (c) each additional track having associated therewith a respective additional first sensor, each additional first sensor being operable to detect when a product moved on the respective additional track with which that additional first sensor is associated has arrived at the target position in the housing along the conveyor route.

3. The test device of claim 1 further including a second sensor operable to monitor a test position spaced apart from the target position along the conveyor route.

4. The test device of claim 3 wherein the second sensor includes a separate sensor for each track.

5. The test device of claim 3 wherein the test position lies within the housing.

6. The test device of claim 5 wherein the at least one closeable opening includes an input opening and the test position lies within the housing adjacent to the input opening.

7. The test device of claim 5 wherein the distance between the target position and the test position is selected to be greater than a length along the conveyor route to be measured for one of the products.

8. The test device of claim 1 wherein each track is further associated with a respective second means of propulsion which is operable separately from the respective first means of propulsion for that track, each respective second means of propulsion being located outside of the housing and being operable for moving products on the respective track along the conveyor route to the housing.

9. The test device of claim 1 wherein each track is further associated with a second means of propulsion which is operable separately from each first means of propulsion, the second means of propulsion being located outside of the housing and being operable for moving products on the tracks jointly along the conveyor route to the housing.

10. The test device of claim 1 further including a scale operable for recording a weight of the products.

11. The test device of claim 1 wherein the respective first means of propulsion for each respective track is selectively couplable to a drive shared with both tracks for conveying the products along a selectable one of the tracks.

12. A process of operating a test device which includes a source of radiation for irradiating products and a housing with at least one closeable opening, the process including:

(a) conveying the products into the housing in a transport direction along each of at least two tracks extending along a conveyor route, each track being associated with a respective first means of propulsion in the housing, each respective first means of propulsion being operable to convey a respective one of the products within the housing along the respective track with which that respective first means of propulsion is associated;

(b) monitoring a target position on each track with a respective first sensor associated the respective track, each first sensor being operable to detect when a product on the respective track with which that first sensor is associated has arrived at the target position in the housing along the conveyor route; and (c) in response to a respective first sensor detecting that a product on the track associated with that respective first sensor has reached the target position, interrupting the movement along the track associated with that respective first sensor.

13. The process of claim 12 further including:
(a) continuing to monitor the target position on each track for which movement has not yet been interrupted; and
(b) for each such track for which movement has not yet been interrupted, interrupting the movement along that respective track in response to a respective first sensor associated with that track detecting that a product on that track has reached the target position.

14. The process of claim 12 further including, after movement has been interrupted on a respective track in response to the first sensor associated with that track detecting the product on that track reaching the target position, moving that detected product in a direction opposite to the transport direction until that product is no longer detected by the respective first sensor.

15. The process of claim 12 further including monitoring for (i) an arrival of a respective product on any of the tracks at a test position spaced apart from the target position along the conveyor route or for (ii) a departure of a respective product on any of the tracks from the test position.

16. The process of claim 15 wherein the monitoring for the arrival or the departure is performed with a second sensor adapted to monitor all of the tracks jointly.

17. The process of claim 15 wherein the monitoring for the arrival or the departure is performed with a second sensor arrangement including a different respective second sensor for each respective track, each respective second sensor adapted to monitor a respective one of the tracks with which that respective second sensor is associated.

18. The process of claim 15 further including controlling a bulkhead operable to selectively close an opening to the housing when no product is located on any of the tracks at the test position.

19. The process of claim 12 further including conveying the products on each of the at least two tracks within the housing so that the products are moved individually or in groups through an x-ray beam provided within the housing.

* * * * *